United States Patent [19]

Flemming et al.

[11] Patent Number: 5,589,650

[45] Date of Patent: Dec. 31, 1996

[54] APPARATUS AND METHOD FOR DEFINING MOLDING TECHNOLOGICAL PROPERTIES OF MOLDING SUBSTANCES IN CASTING WORKS

[75] Inventors: Eckardt Flemming; Werner Tilch, both of Freiberg; Thomas Schuszter, Augsburg; Marian Ivanov, Freiberg; Paul Eirich, Handheim, all of Germany

[73] Assignee: Maschinenfabrik Gustav Eirich, Germany

[21] Appl. No.: 230,892

[22] Filed: Apr. 21, 1994

[30] Foreign Application Priority Data

Apr. 21, 1993 [DE] Germany ............................ 43 12 939.0
Apr. 21, 1993 [DE] Germany ............................ 43 12 938.2

[51] Int. Cl.$^6$ .......................... G01N 33/38; G01N 29/18; G01N 29/00; G01N 29/10
[52] U.S. Cl. ........................... 73/866; 73/597; 164/456
[58] Field of Search .......................... 73/632, 866, 803, 73/818, 594, 597, 598, 599, 600, 602, 628, 644, 645, 646; 164/456

[56] References Cited

U.S. PATENT DOCUMENTS

| | | | |
|---|---|---|---|
| 2,791,120 | 5/1957 | Dietert et al. ............................. | 73/866 X |
| 3,141,129 | 7/1964 | Dietert ............................. | 164/456 X |
| 3,156,112 | 11/1964 | Dietert ............................. | 73/866 X |
| 3,181,370 | 5/1965 | Dietert ............................. | 73/866 |
| 3,412,325 | 11/1968 | Soderling ............................. | 164/456 X |
| 4,141,404 | 2/1979 | McMullen ............................. | 164/456 |
| 4,550,768 | 11/1985 | McMullan et al. ............................. | 73/866 X |
| 4,856,335 | 8/1989 | Tornberg ............................. | 73/597 |
| 5,224,381 | 7/1993 | Sandoz et al. ............................. | 73/597 |

FOREIGN PATENT DOCUMENTS

| | | | |
|---|---|---|---|
| 0506409 | 9/1992 | European Pat. Off. . | |
| 3220662 | 12/1983 | Germany ............................. | 164/456 |
| 253197 | 1/1988 | Germany ............................. | 164/456 |
| 275822 | 2/1990 | Germany ............................. | 164/456 |
| 3932 | 2/1973 | Japan ............................. | 73/632 |
| 278934 | 11/1989 | Japan ............................. | 164/456 |
| 1543285 | 2/1990 | U.S.S.R. ............................. | 73/866 |

OTHER PUBLICATIONS

Derwent Abstract SU 150 3991, Aug. 30, 1989.

Primary Examiner—Thomas P. Noland
Attorney, Agent, or Firm—Michael L. Dunn

[57] ABSTRACT

The invention relates to a process and an apparatus for defining the properties and composition of molding sand in casting works, wherein some of the properties are defined in a test sleeve which receives a molding sand sample. In order to create a process or a testing method which makes it possible to more quickly and easily determine the properties of the molding sand which are essential for purposeful use, the invention proposes to take an ultrasonic measurement of the sample of molding sand, wherein, independently of this, at least one further property of the sample of molding sand is measured or defined, and the combined results of the ultrasonic measurement and further measurement are used to define the properties and composition of the sample. In order to create an apparatus which makes it faster and simpler to define the properties of the molding sand which are important for purposeful application, at least one ultrasonic transducer is provided at an end of the sample.

25 Claims, 3 Drawing Sheets

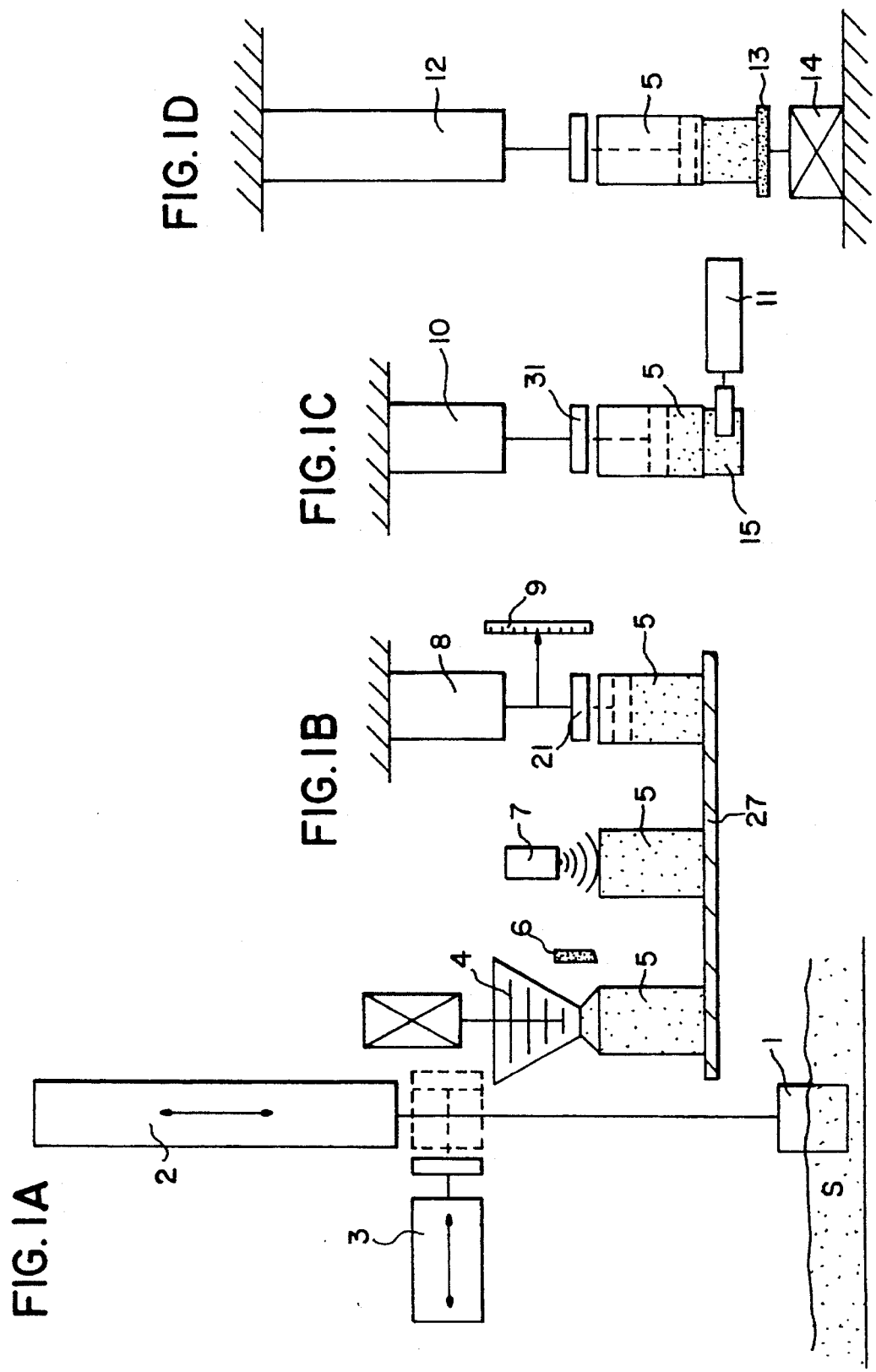

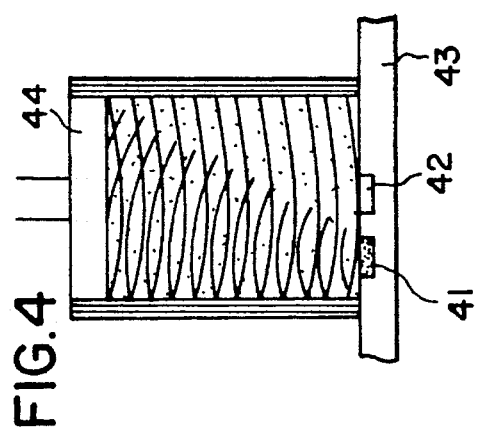
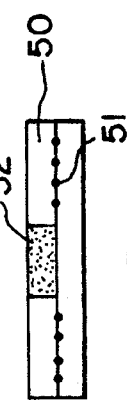
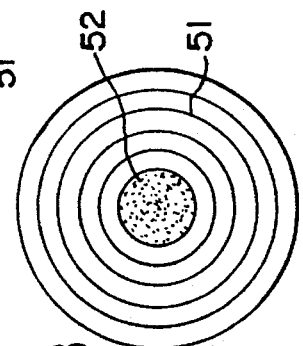
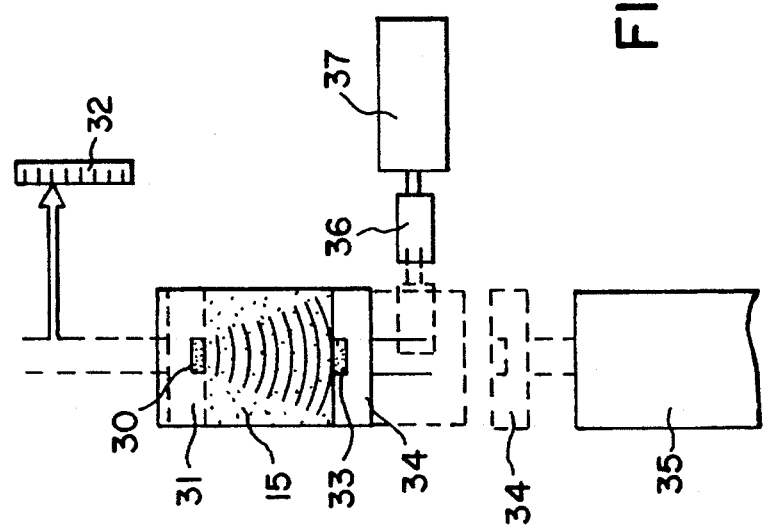
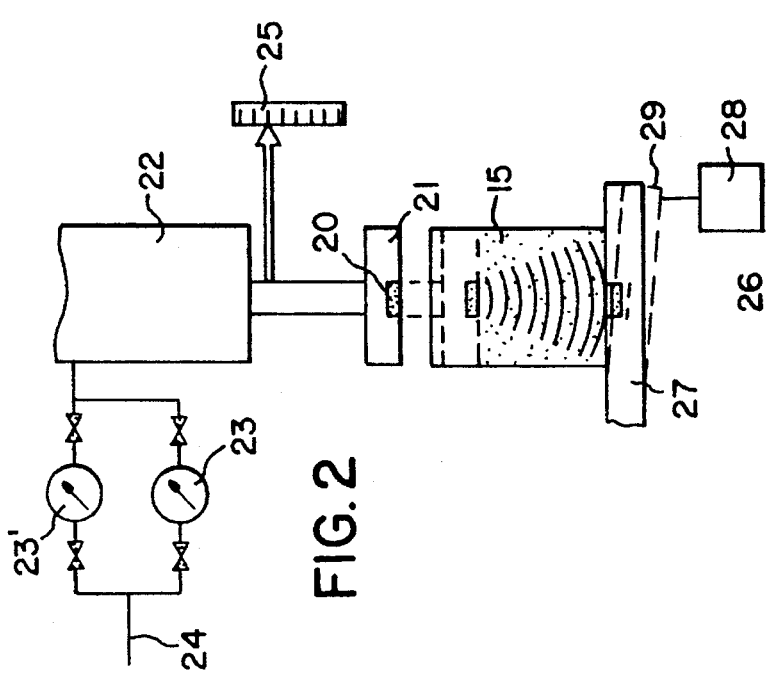

APPARATUS AND METHOD FOR DEFINING MOLDING TECHNOLOGICAL PROPERTIES OF MOLDING SUBSTANCES IN CASTING WORKS

BRIEF DESCRIPTION OF THE DRAWINGS

FIGS. 1A through 1D show an automatic apparatus for testing molding sand at a plurality of stations I–IV respectively.

FIGS. 2 to 4 show various arrangements of ultrasonic converters on stations of an apparatus for testing moulding sand.

FIGS. 5A and 5B show an ultrasonic measuring stamp with a heating device from top and cross-sectional side views.

BACKGROUND OF THE INVENTION

Figure 6:
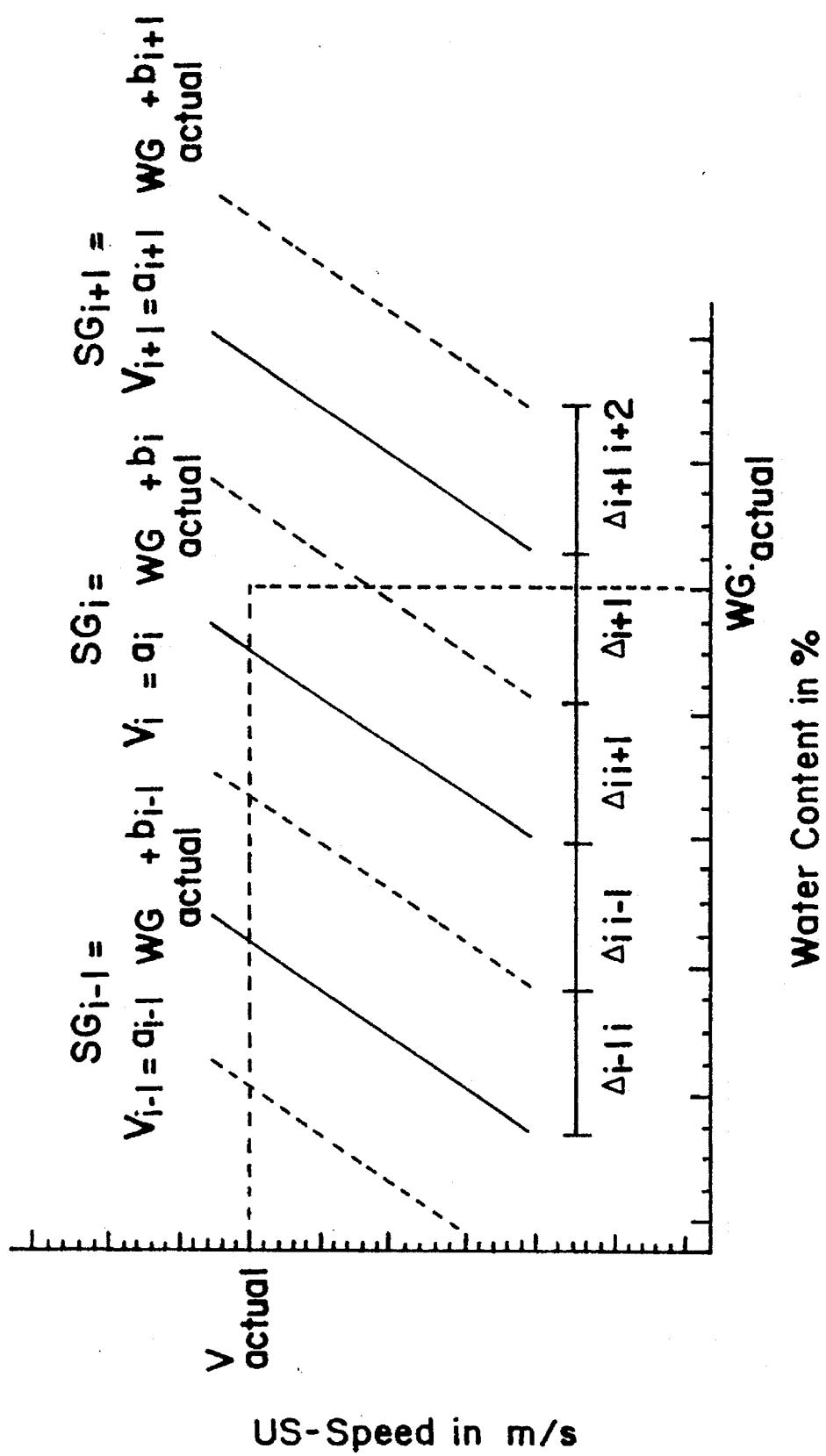
FIG. 6 is a graph showing the connection between ultrasonic speed, water content and further properties of the sample.

The invention relates to a testing method for defining the properties of moulding material systems in casting works and their components by measuring the elastic and non-elastic properties (propagation and absorption of elastic waves) by means of ultrasound, incorporating further physical and/or technical-technological characteristic values. The ease with which the measurements are made by way of this testing method (no destruction, speed, possibility of automation) permits new testing systems to be developed for testing the moulding material and also for monitoring and controlling quality in the preparation and manufacture of the mould and core.

Further, the present invention relates to an apparatus for finding out the characteristics of casting works moulding sand, in particular for defining the properties and/or composition of casting works moulding sand, having a sample-taking device and a test sleeve which receives a sample of moulding sand, preferably in the form of a precompacted testing body.

The properties in respect of the processing technology of a moulding material are representative of a combination of material-related factors, technological factors and equipment-related factors, each of which have an influence on the preparation-, moulding- and/or casting process. The moulding material composition—moulding material quality—moulding quality chain purposefully influences the quality of the cast article. To that end, testing characteristic values are involved which have a direct influence on changes in the material with effects on the moulding technology related properties.

The conventional method of testing moulding materials often places the quality of the material under conditions which are close to practice. A relatively large amount of time is involved which restricts the "sensitivity of the reaction" to disturbance magnitudes, and the meaningfulness of statements made about it is likely to be deficient.

Methods in applied physics which have developed on the principle of advanced measuring technology enable a detailed definition to be made of the physical properties and their relationship, above all, to active physical and also technical-technological parameters. Taking into consideration the conditions specific to casting, such processes can be used for practical implementation of moulding material testing and moulding material controlling methods, and they have considerable advantages over conventional testing processes (e.g. possibilities for automatic realisation, greatly reduced testing times, inter alia). This makes itself very apparent when moisture is measured in clay bonded moulding materials by way of an electromagnetic process, or when the hardening condition is measured during manufacture of the core by way of an electric process.

Moulding technology-related properties of clay bonded moulding materials are mainly defined by measuring compressibility and compression strength, wherein these values are, in turn, dependent on water content, granulometric characteristic values (sludge content) and bindable proportion of clay (active clay). The most customary processes for defining these characteristic values are the processes used in many casting works in the form of analyses made of the sieve, sedimentation and adsorption. Such testing methods are suitable enough, but they are costly, particularly in terms of time, and they cannot be automated or used with attendant monitoring of the process. With previously known automatic systems for controlling optimum moulding material properties, measurements are taken of the compressibility and water content, of the compression strength and shearing strength or deformation limit. These measurements, with the exception of that for defining water content, are taken after the moulding material has been mixed, and on the basis of these measurements the measured amounts of clay and water are worked out for the following mixing charge. One drawback with systems such as this is that no consideration is taken, or insufficient consideration is taken, of fluctuations in the sludge part and in the active clay part which occur during operation, since the measured amounts for the current mixing charge are calculated from the measured values of previous charges. To overcome this problem, process data is used (e.g. sand/casting ratio and amount of core placed in the mould). However, associating this data with the individual mixing charges is unreliable (e.g. discharge of core sand from the circulation of moulding material, infiltration of old casting works sands during transportation), which means that in practice the values to be worked with are inaccurate, and this naturally has an unfavourable effect on the success of controlling the operation.

One possible solution which provides for attendant definition of the quality of old casting works sand is disclosed in DD-PS 253197. This proposes a process for on-line definition of the water-, sludge- and active clay content in the old sand of the casting works, wherein the attenuation of Röntgen- or gamma radiation and ultrasonic speed are determined on samples of moulding material. Transposition of this measuring concept fails because of the increased technical requirements imposed on the radiometric measurement operation (safety requirements, maintenance costs).

In controlling uniformity and quality of organic binding agents and of water glass bonded moulding materials, the mechanical properties of the testing bodies for such moulding material mixtures are defined. It is mainly a question of testing bending strength, but also other measurements of strength are involved (e.g. shearing strength and compression strength). Also, rheological properties are examined (e.g. deformation testing, duration of processability) of the moulding material mixes. Since defining the strength obtainable through hardening is a fundamental criterion for the quality of the moulding material, a hardening feature is usually determined, wherein the strength obtained is represented in dependency on the duration of the hardening process. In sito measurements using these testing methods are not possible. Automation or on-line execution of monitoring and controlling operations is undesirable, or are not possible, because of the cost.

DE-PS 3152073 discloses one proposal for carrying out attendant definition and control of the quality of the core sand. According to this proposal, the necessary hardening time is calculated by measuring the magnitude of electrical conductivity on a testing body before and after it hardens, and the variation range of that magnitude is simultaneously defined. The magnitude of electrical conductivity corresponds to a hardness degree for the core which is such that it ensures that the core attains previously set down strength properties, and is thus used as a yardstick for controlling core quality. One drawback with this method should be mentioned, namely the lack of flexibility in assessing the electrophysical properties with a view to application to other moulding material systems.

At present, in order to assess the effect of regeneration, reference is made exclusively to the characteristic values of old sand in casting works: "washable substance" and "loss on ignition". The testing methods for defining these characteristic values are known from conventional testing of clay bonded moulding materials, and they have all the advantages and disadvantages of those measuring processes, see above.

Apparatus of the above mentioned kind which is already highly automated in many instances is in widespread use in casting works. Therein, a cylindrical test sleeve which is open at both ends, but which is initially without application of pressure, is filled with moulding sand. To this end, the open underside of the test sleeve is, at least temporarily, closed by a pressure plate or the like. The sleeve which is filled in this way is then conveyed to a compressing station where a stamp is pressed down onto the moulding sand from the open top side of the test sleeve, and compresses the mouldlng sand. By measuring the path which the pressure stamp covers In the test sleeve when this takes place, it is possible to define the compressibility of the moulding sand.

In another station it is possible to measure the shearing strength of the compressed testing body, by the testing body being pressed out of the sleeve by the pressure stamp or another stamp, for example, after the pressure plate which initially closes the sleeve has been removed, or after the test sleeve with the testing body has been taken from the pressure plate. The part of the testing body projecting from the test sleeve can then be sheared off by a laterally attacking fork, wherein the forces which act upon the fork are measured. In addition to measuring the shearing strength, further automatic measuring stations can be provided, for example for defining moisture and other parameters with the aid of various sensors and including contact-free measuring methods or measuring methods which operate by making contact.

However, some of the measuring- and investigational methods are relatively costly, particularly if indications are to be given on the composition of the moulding sand, with the content of active bentonite and sludges being the main interest. The content of active bentonite and of sludges has a considerable influence upon the moulding technological properties of the moulding sand. Therefore, there is a need for an apparatus which makes it possible to define, in a quicker and simpler manner, the properties of the moulding sand which are important for purposeful application.

BRIEF DESCRIPTION OF THE INVENTION

The object of the invention is a testing process for defining the properties of moulding material systems in casting works, and of their components, which satisfies the requirements of providing a guarantee of quality with flexible, high output moulding- and core manufacturing installations, particularly with a view to attendant monitoring and control. The object of the invention should be able to be used for the many different types of casting works moulding material systems by determining physical properties and their relationship to technical-technological parameters with the minimum amount of expense in terms of technical factors and time factors. Therein, it should be possible to make accurate statements about the properties of the moulding materials (composition, strength behaviour) by determining ultrasonic characteristic values on specific testing bodies and on moulds and cores, permitting the quality of the moulding material to be monitored and controlled.

The aim of the invention is to create a testing method for defining the properties of casting works moulding material systems and their components, on the basis of which testing processes are developed for individual casting works moulding material systems, and are used to guarantee quality with flexible, moulding- and core manufacturing installations of high output.

According to the invention, this problem is solved in that the properties of casting works moulding material systems and their components are defined by measuring the elastic and non-elastic properties (propagation and absorption of elastic waves) by means of ultrasound, incorporating further physical characteristic values (e.g. water content or content of binding agents and hardeners), and/or technical-technological characteristic values (e.g. compressibility, duration of hardening operation, inter alia). The ultrasonic speed is defined on specific samples or in site under specific coupling conditions (coupling pressure and -duration) and at a given ultrasonic frequency. According to the invention, the following definition processes are developed in dependency on the casting works moulding material system to be investigated. Regarding the apparatus, the above problem is solved in that an ultrasonic converter is provided on at least one surface which delimits the testing body consisting of compressed moulding sand.

DETAILED DESCRIPTION OF THE INVENTION

The compressibility, water content and ultrasonic speed depends on the moulding material or the old sand of the casting works, and the granulemetric properties (sludge content or fine pans) and active clay content are determined as a result.

To measure the corresponding magnitudes, a sample is taken of the moulding material or old sand of the casting works, is shaken into a shape of specific volume, and is condensed at a given force (definition of compressibility). The condensed sample is subjected to a through-transmission ultrasonic testing technique under specific coupling conditions (coupling pressure and coupling duration) and at a given ultrasonic frequency. Therein, the ultrasonic speed of the sample is measured. The water content can be defined during manufacture of the sample, or beforehand. The granulemetric characteristic values (sludge content and fine proportions) are determined by the equation:

granulemetric characteristic values=f(water content, ultrasonic speed).

The active clay content is determined, under the condition of known granulemetric characteristic values, by the equation:

Active clay=f(compressibility, ultrasonic speed)

or

Active clay=f(water content, compressibility).

To determine the granulemetric characteristic values and active clay content, compensating straight lines are defined beforehand by way of test mixtures of known composition taken from the moulding material to be investigated, and are used in accordance with conventional interpolation methods. The granulemetric characteristic values determined and the active clay content can, together with the water content and compressibility, be used as control magnitudes for composing the charge of mouldlng material during preparation.

A sample is taken of the freshly prepared moulding material mixture. Depending on the solidification method employed, the sample is shaken into a shape of defined volume before or shortly after entering the solidification process, and is condensed at a given force. The condensed sample is subjected to a through-transmission ultrasonic testing technique under specific coupling conditions (coupling pressure and -duration) and at a given ultrasonic frequency. Therein, the ultrasonic speed of the sample is measured. The ultrasonic speed is measured continually and until the hardening reaction has ended. The ultrasonic speed values which are recorded in this way are represented in dependency on the duration of the hardening process. As hardening advances, the ultrasonic speed increases. The trend of the curve showing ultrasonic speed-hardening time is a yardstick for the disturbance variables which affect the hardening process (e.g. sludge content of quartz sand). The ultrasonic speed at a specific time during hardening corresponds to the strength level attained, and thus replaces the tests on strength used with conventional testing methods.

Recording the hardening feature mentioned initially can also be done with the mould parts or core parts. It thus shows that the given strength properties have been reached. In addition, any cracks occurring in the sample of the mould- or core part which has been subjected to the through-transmission technique of ultrasonic testing are easy to see by a drastic reduction in the ultrasonic speed.

When preparing clay bonded moulding materials, the mould technology-related properties have to be corrected by adding measured amounts of water, base moulding materials and clay to the old sand of the casting works. However, these properties can only be controlled if consideration is taken of fluctuations, occurring during operation, in the sludge content, and the water content is then adjusted accordingly. In addition, the current part of active clay is taken into consideration, and the strength is set by purposefully measuring amounts of clay.

With the process according to the present invention, a sample-taking device upstream of the mixer for old sand of the casting works is used to remove moulding material from the mixer or downstream of the mixer, and to provide a constant sample volume. Condensing then takes place using a piston. A sensor, operating on the basis of the dielectric constant, on the condensed sample is used to determine the water content of the casting works old sand or of the moulding material. The water content is determined by incorporating the temperature of the old sand of the casting works or of the moulding material which is measured by a temperature probe. When testing the moulding material, the water content can also be defined during mixing. In a next step, ultrasonic measuring heads are coupled to the sample under specific coupling conditions (coupling pressure and coupling duration). Therein, an inductive path recorder is used to calculate the depth of the sample, and, from it, the compressibility. The sample is then subjected to a through-transmission ultrasonic testing technique at a given ultrasonic frequency, and the ultrasonic running time is calculated. The ultrasonic speed is determined from the running time, including the sample depth.

By virtue of an ultrasonic converter of this kind it is possible to measure the propagation speed and the attenuation of ultrasonic waves in the moulding sand body, and to draw from this conclusions about the elastic and non-elastic properties of the moulding sand which either serve directly as properties characterising suitability of the moulding sand for specific purposes, or which, on the basis of experimental values or appropriate series of tests, allow conclusions to be drawn about the content of active bentonire and sludges. It has been shown that the connection between ultrasonic speed and -attenuation under suitable testing conditions makes it possible to draw definite conclusions about the suitability of the moulding sand for use in specific applications, and, in particular, allows statements to be made about which components still have to be added to the moulding sand in order to impart to it the desired properties. Examples of additives which can be considered are the afore-mentioned materials, active bentonite and sludges and also new sand and water. Therefore, the ultrasonic measurements also indirectly enable conclusions to be made about the composition of the moulding sand which can then be altered in the desired way. Therein, the ultrasonic measurement is a very fast measuring method which involves little expense in terms of apparatus, particularly in comparison with other quantitative methods of analysis which are otherwise necessary in order to be able to draw reliable conclusions about the composition of the moulding sand.

One embodiment of the invention is preferred, wherein two ultrasonic converters are arranged on two oppositely disposed sides of the testing body. One of these converters can then act as an emitter, and the other, oppositely disposed, converter acts as a receiver, wherein the running time through the testing body, the change in amplitude when passing through the testing body and possibly other phase jumps etc. are detected. However, it is also possible to take corresponding measurements using only one single ultrasonic converter in which the converter only emits one short pulse and then receives the echoes sent back from the testing body which are analysed in an appropriate electronic device. Expediently, in such a case, a surface which properly reflects the ultrasound is arranged on the side of the testing body oppositely disposed to the converter.

In the preferred embodiment, the test sleeve is substantially cylindrical, wherein the ultrasonic converter(s) is/are arranged on plates or stamps which are placed on the ends of the cylindrical testing body, Therein, one of these surfaces or plates can belong to a compressing stamp, whilst the oppositely disposed plate is a pressure plate or a counter-pressure plate, wherein the stamp and the pressure plate are parts of a compressing testing station. By way of example, a cylindrical testing sleeve can be placed on a pressure plate with both ends of the testing sleeve open, and it is then filled with sieved moulding sand and/or moulding sand from which lumps have been removed, wherein a stripper is responsible for ensuring that the sleeve is filled uniformly exactly up to the edge. In this state, the sleeve is then conveyed to the compressing station, where a stamp which fits into the cylindrical sleeve as closely as possible is placed on the end face of the testing body and is pressed into the sleeve. Therein, the moulding sand is compressed, and the compressibility results from the ratio of the volume of the testing body which results at a given test pressure to the total volume of the test sleeve which was previously subjected to the claims of the moulding sand. Therein, the ultrasonic converter can be arranged directly in the pressure stamp of the compressing testing station, whilst another ultrasonic converter may be arranged in the pressure plate on the bottom of the testing sleeve. It is also expedient therein if the pressure regulating system which sets the testing pressure at which the stamp is pressed onto the sample of sand has at least a two-staged pressure regulator, so that a pressure can be selected for the ultrasound measurement which is independent of the testing pressure provided for the compressing operation, this independent pressure usually being less than the pressure applied to compress the sample.

However, the ultrasonic converters can quite easily be arranged in the surfaces which are independent of the compressing station, particularly if there is a risk that the pressure applied during the compressing operation will damage the surfaces of the converter which come into contact with the sand, or if a suitable protective layer cannot be applied, or if the measured result would be too greatly falsified.

For the sake of simplicity, in such a case, the ultrasonic converter could be arranged on a stamp and an appropriate counter-plate of a station for measuring shearing strength of the testing body. To measure shearing strength, the testing body is actually pressed out of the test sleeve by a stamp, wherein the pressure to be applied to do this is considerably less than that required for the compression operation. The desired ultrasonic measurement could be made before the testing body is pushed out of the sleeve, when the corresponding stamp and a suitable counter-plate are being placed on the underside of the sleeve, so that the testing body is only expelled from the bottom of the sleeve with the sleeve firmly held and the stamp of the shearing strength station pressed down, wherein clearly the counter-plate has to be moved with it or has been removed beforehand.

When the shearing strength is measured, a fork then moves laterally towards the testing body and measures the forces occurring during the shearing off operation.

With another embodiment of the invention, two ultrasonic converters are arranged adjacently to each other on one and the same surface or on surfaces which are close together, wherein the one ultrasonic converter acts as an emitter and the other acts as a receiver. In this case too it is again expedient if a surface which properly reflects the ultrasound is arranged on the side of the testing body which is oppositely disposed to the ultrasonic converters.

DETAILED DESCRIPTION

First of all, an example of a conventional apparatus for testing moulding sand will be described with the aid of FIGS. 1A–1D, and this apparatus can advantageously be complemented by the features of the present invention.

In FIG. 1A, a sample-taking device 1 can be seen which takes a sample of sand from a sand bed S. The sample-taking device 1 is actuated by a lifting cylinder 2, wherein the sample of sand is lifted up towards a discharge cylinder 3 and is thence emptied in a chopper funnel 4 or onto a corresponding sieve. Thence, the sand is filled into a cylindrical test sleeve 5 which is arranged under the chopper funnel 4 and which stands on a base 27, the test sleeve being open at the top and bottom, but being closed at its lower side by the base plate 27. The amount of sand which is placed by the sample-taking device 1 into the funnel 4 or onto a corresponding sieve is such that the test sleeve 5 is well filled. The sleeve 5 is then moved to the right on the plate 27, and the plate 27 may possibly be in the form of a rotary table or a jointed conveyer belt or the like which takes the sleeve to a filling condition measuring means 7. On the way to the filling condition measuring means 7, the sleeve 5 passes under a stripper 6 which strips away excess sand which has accumulated above the upper edge of the test sleeve 5, so that the surface of the sand in the test sleeve 5 ends exactly with the top edge of the test sleeve 5. This is checked by the filling condition measuring means 7. The test sleeve 5 filled in this way is then advanced to a compressing station II, in which a compressing stamp 21 which is dimensioned in accordance with the internal size of the test sleeve 5 is lowered onto the surface of the sand in the test sleeve 5 by way of a hydraulic compressing cylinder 8. The sand is loaded by the stamp 21 at a pressure which is set exactly by the hydraulic device 8, wherein the compressibility results from the change in volume of the sand, i.e. as a concrete result of the path which the stamp 21 makes in the test cylinder 5, in relation to the height of the testing cylinder. A suitable path measuring device 9 is provided in the compressing station 2.

It will be appreciated that the plate 27 acts as a counter-pressure plate and is supported appropriately in the compressing station.

In a way which is yet to be described, an ultrasonic measuring system can be arranged in this compressing station, as shown in FIG. 1B.

The sleeve 5 with the compressed testing body is then advanced to a station, as shown in FIG. 1C, for measuring the shearing strength of the testing body. To this end, the testing body 15 is pressed by another stamp 21 a little further down out of the test sleeve 5, and the part of the testing body 15 which projects from the test sleeve 5 is then sheared off by a fork 11 in the lateral extent, wherein the forces required for this are measured on the fork or fork holding means. Instead of measuring the shearing strength it is also possible to measure the compression strength, as shown in at the station shown in FIG. 1D. Therein, a stamp driven by the cylinder 12 likewise presses the testing body 15 completely out of the sleeve 5, wherein the testing body is placed on a counter-pressure plate 13 and is crushed under the continuing backwards movement of the stamp. The forces acting on the counter-pressure plate 13 are determined by a force receiving means 14.

FIG. 2 illustrates the way in which it is possible to realise an ultrasonic measuring system, on the afore-described compressing station shown in FIG. 1B. To this end, the front face of the compressing stamp 21 which makes contact with the sand has a recess in which an ultrasonic converter 20 fits, so that its front face ends flush with the front face of the stamp 21. Electrical connections on the reverse of the ultrasonic converter are not shown in FIG. 2. However, they can be wired in per se known manner through bores in the back of the stamp 21.

An ultrasonic converter 26 is accommodated in a recess which fits it in the counter-pressure plate 27 in a similar way to the stamp 21, and the surface of the ultrasonic converter which faces the testing body 15 is likewise flush with the surface of the plate 27. The counter-pressure plate 27 can, as indicated by a broken line, be pivoted down into the position 29 by means of a lifting element 28, so that the testing body 15 in the test sleeve which may be fixed to a carrier arm can be further transported after the measurements have been completed in the compressing station, without contacting the plate 27, in order to prevent any wear of the surface of the converter 26 due to friction.

The hydraulic cylinder 22 can be loaded with pressure by way of two different pressure control valves 23, 23', via the supply line 24. One of the two pressure control valves 23, 23' becomes operative to measure compressibility, wherein the path along which the stamp 21 penetrates into the sleeve 5 can be read off on the scale 25 or can also be detected automatically. The other pressure control valve 23' is then actuated, or can be detected automatically. The other pressure control valve 23' is then activated which provides somewhat less pressure in the hydraulic cylinder 22, so that the stamp 21 presses against the surface of the testing body 15 with somewhat less pressure. In this condition, the ultrasonic measurement is taken on the testing body, wherein, for example, the converter 20 acts as the emitter and the converter 26 acts as the receiver. The electronic measuring device for these ultrasonic converters is known theoretically and therefore does not need to be described. In particular, the running time of the ultrasonic impulses through the testing body 15 are measured, wherein it is also possible to calculate the ultrasonic speed from the depth of the testing body 15 which results from the depth of the test sleeve 5 and the compression path of the stamp 21. It is also possible to determine the attenuation of the ultrasonic wave, preferably by detecting one or more successive echoes of a short ultrasonic impulse which resound back and forth between the surfaces of the stamp 21 and the surface of the counter-pressure plate 27.

After the ultrasonic measurement is complete, the stamp 21 is withdrawn from the sleeve 5 with the ultrasonic converter 20, and the counter-pressure plate 27 is pivoted or bent down, so that the testing body 15 with the test sleeve 5 can be conveyed to the next station in contact-free manner.

FIG. 3 shows a station for measuring the shearing strength of the testing body 15, wherein this station is likewise complemented by an ultrasonic measuring device. The testing body 15 which may have been pre-compressed in a station, as shown in FIG. 1B, is transferred in the test sleeve 5 to the station for measuring shearing strength. Before measuring shearing strength a stamp 34 is first of all pressed against the bottom end face of the cylindrical testing body, whilst a stamp 31 is lowered from the top into the test sleeve 5 and onto the surface of the testing body 15. Both stamps 31 and 34 have an ultrasonic converter 30, 33 which ends flush with its surface, the wiring of which ultrasonic converters and electrical connections need not be shown. The stamp 31 is lowered onto the surface of the sand at a specific pressure, since uniform pressure makes it easier to make comparisons between the measurement results, even though this condition cannot be abandoned provided that the pressure-dependency of these measured results has been detected in a corresponding series of tests.

The scale 32 is helpful in finding out the height of the testing body 15, in order to establish the path of movement of the ultrasonic impulse through the testing body 15. The height of the testing body can, however, be taken as the measured result from the previous compressing station.

After the ultrasonic measurement has been completed, the stamp 34 is lowered down further by way of the hydraulic cylinder 35, whilst the stamp 31 presses the testing body 15 through a given extent down and out of the test sleeve 15, so that it can be held by the shearing fork 36. When it shears off the part of the testing body 15 projecting downwardly out of the test sleeve 5, the feed system 37 for the shearing fork picks up the forces which act upon the fork 36.

Similarly, the ultrasonic converters can also be provided in a station for measuring compressive strength, as shown at the bottom FIG. 1D. In this case too, an ultrasonic converter could be provided in the stamp 13 and also in the stamp which can be lowered from the top, wherein it is expedient if the stamp 13 ought to be moved far enough down for it to close the bottom side of the test sleeve 5. Instead, however, a counter-pressure plate can also be arranged on the underside of the sleeve 5 independently of the stamp 13, this sleeve receiving the ultrasonic converter and possibly being able to be pivoted down from the sleeve 5.

FIG. 4 shows a variant where two ultrasonic converters 41, 42 are arranged in a counter-pressure plate 43 on the underside of a testing body 15. The ultrasonic waves which emanate from the ultrasonic converter 41 are reflected both by the walls of the test sleeve 15, but mainly also by a stamp 44 which rests on the upper side of the testing body 15, and received by the converter 42. The ultrasonic speed is calculated, in turn, from the running time and the depth of the testing body. In a further variant, the converters 41 and 42 could be identical, i.e. one single converter 41 would act as both a transmitter and a receiver, which is possible without further ado with per se known electronic switching of converter connections.

FIG. 5 shows a stamp or a plate 50 in which an ultrasonic converter 52 is received in such a way that its surface ends flush with the surface of the plate 50. A heating coil 51 which embraces the ultrasonic converter 52 is simultaneously placed inside the plate 50, by means of which heating coil the plate 50 can be heated, so that the moulding sand is prevented from adhering, which could happen if condensation was produced on the stamps or plates due to changes in pressure load.

The apparatus according to the invention, together with the already known testing devices such as compressing-, shearing strength- and compressive strength-measuring stations makes it possible to detect all the important properties of a moulding sand in a way which is a more thorough and faster in comparison with previously known automated testing apparatus. In particular, combining the ultrasonic measurement with the other testing methods mentioned hereinabove eliminates the need for a quantitative analysis of the moulding sand composition, since the ultrasonic measurements, at least in conjunction with the other properties which are easy to measure, such as compressibility and shearing strength, already give enough information on the composition of the moulding sand. Therein, suitable series of measurements are all that are needed to find out the connections between the ultrasonic results and the respective composition, so that it is then possible to draw conclusions about the composition on the basis of the ultrasonic results. Therein, consideration should, of course, be taken of the fact that different types of binding agents exist in moulding sands.

The apparatus according to the invention can, of course, also be used in other production procedures, e.g. for ceramics masses, soil-mechanics testing, building materials, etc.

The data for the purpose of providing attendant control of the moulding-technological properties of the moulding material system is derived from the three pertinent values: water content, compressibility and ultrasonic speed:

Sludge content:

The ultrasonic speed gives information on the sludge content by way of compensating straight lines in conjunction with the water content. FIG. 6. The compensating straight lines are established by way of test mixtures of known composition from the moulding material system to be investigated. Therein, the conventional interpolation methods are used:

FIG. 6: Definition of Sludge Content

Measured values $WG_{actual}$, $V_{actual}$

Compensating straight lines: $SG_{i-1}=V_{i-1}*WG_{actual}+b_{i-1}$; $SG_i=V_i=a_i*WG_{actual}+b_i$; $SG_{i+1}=V_{i+1}=a_{i-1}*WG_{actual}+b_{b+1}$ Spread bands between the individual compensating straight lines: $\Delta_{i-1i}=\Delta_{ii-1}=(V_{i-1}-V_i)/2$ $\Delta_{i+1i}=\Delta_{ii+1}=(V_i-V_{i+1})/2$ Comparison: $V_i-\Delta_{ii+1}<V_{actual}<V_i+\Delta_{ii-1}$ Conclusion: $SG_{actual}=SG_i$ Definition of Active Clay The compressibility determines the active clay content by way of compensating straight lines in conjunction with the water content and with the known sludge content. When drawing up the compensating straight lines, a compensation factor necessitated by the sludge material is additionally determined.

After calculating the actual state, a comparison is made with nominal values. The process calculator gives corresponding setting pulses to the dosing device, and the mixing charge is put together from old sand from the casting works, basic moulding material, clay and water.

What is claimed is:

1. A process for determining properties of compositions for making molds for the purpose of assessing the quality of the composition, wherein the determination is carded out by first compacting a sample of the composition and determining the length of such compacted sample along at least one dimension and measuring propagation and absorption of elastic waves by means of ultrasound along said dimension and using such measurements in combination with at least one other property of the composition to calculate additional properties.

2. The process of claim 1 for defining quality of a composition of clay bonded molding materials, wherein ultrasonic speed, moisture, temperature and compressability are measured to calculate active clay content and sludge content of the molding material.

3. The process of claim 2, wherein solidification and determination of state characteristics are determined from measuring changes in ultrasonic characteristic values.

4. The process of claim 2, wherein the quality of regenerated mold forming material is calculated by determining a proportion of disturbance variables using measured ultrasonic values.

5. A process for defining properties and composition of molding sand which comprises:
   a) introducing a sample of the molding sand into a test sleeve having a side wall and opposing ends;
   b) compressing the sample within said sleeve by means of a stamp and pressure plate which move toward each other to compress the sample within the sleeve to form a compressed sample having opposing ends;
   c) after compressing the sample measuring a length of the sample between the stamp and pressure plate;
   d) measuring ultrasonic speed through the sample by means of at least one ultrasonic transducer located at one of said ends;
   e) measuring at least one other property of the sample selected from the group consisting of moisture content, compressibility, ultrasound attenuation and temperature; and
   f) using all of such measurements to define the properties of the sample.

6. A process according to claim 5 wherein absorption properties of the sample are defined on the basis of the ultrasonic speed and measured ultrasonic amplitudes.

7. A process according to claim 5, characterized in that phase and amplitude of ultrasonic waves are defined through reflection on one or more surfaces of the sample.

8. A process according to claim 5, wherein two ultrasonic transducers are provided, arranged on oppositely disposed sides of the sample, one side of which acts as an ultrasonic emitter and the other of which acts as an ultrasonic receiver.

9. A process according to claim 5, wherein two ultrasonic transducers are provided adjacently to each other on a surface of the sample, at least one of which acts as a receiver for reflected ultrasonic waves.

10. A process according to claim 5, wherein the ultrasonic measurement is carded out with an adjustable coupling pressure of said at least one ultrasonic transducer on the sample.

11. A process according to claim 5, wherein in addition to the ultrasonic measurement, a further measured magnitude is determined in the form of the compressibility of the sample.

12. A process according to claim 5, wherein, in addition to the ultrasonic measurement, a further physical measured magnitude is determined in the form of the water content of the sample.

13. A process according to claim 12, wherein the composition of the sample is determined on the basis of measured magnitude using calibration tables.

14. A process according to claim 5, wherein in addition to the ultrasonic measurement, a further measured magnitude is determined in the form of the content of binding agents and hardeners in the sample.

15. A process according to claim 5, wherein the composition of the sample is not directly measured but is determined from other measured properties on the basis of a mathematical relation between composition and such other properties.

16. An apparatus for practicing the process of claim 5 for characterizing a sample of casting works molding sand, said apparatus having
   a) a sample-taking device,
   b) test sleeve which receives the sample of molding sand,
   c) the stamp and pressure plate for compressing the sample within the sleeve to form the compressed sample having a first end, a second end and a sidewall defining a testing body,
   d) said at least one ultrasonic transducer provided at the first end of the sample,
   e) means for determining the distance from said first end to said second end, and
   f) means for determining a time of an ultrasonic pulse to pass through the sample between the ends thereof.

17. An apparatus according to claim 16 wherein two ultrasonic transducers are provided on oppositely disposed sides of the testing body.

18. An apparatus according to claim 17 wherein one of the ultrasonic transducers is arranged at an end face of the testing body.

19. An apparatus according to claim 16 wherein the testing body is essentially cylindrical and an ultrasonic transducer is provided in the compressing stamp at one end of the cylindrical body.

20. An apparatus according to claim 19 wherein a pressure regulator is provided which has at least two pressure stages for regulating pressure applied by the compressing stamp.

21. An apparatus according to claim 16 wherein the testing body is essentially cylindrical and an ultrasonic transducer is provided in the pressure plate at one end of the cylindrical body.

22. An apparatus according to claim 16 wherein ultrasonic transducers are distally located from surfaces which receive compressing pressure.

23. An apparatus according to claim 16 wherein the ultrasonic transducer can move to and from the testing body.

24. An apparatus according to claim 16 wherein two ultrasonic transducers are arranged on a surface adjacent to each other and oppositely disposed to a reflecting surface.

25. A process according to claim 5 wherein ultrasonic amplitudes are measured and used to determine non-elastic properties of the sample.

* * * * *

UNITED STATES PATENT AND TRADEMARK OFFICE
CERTIFICATE OF CORRECTION

PATENT NO. : 5,589,650

DATED : December 31, 1996

INVENTOR(S) : FLEMMING ET AL.

It is certified that error appears in the above-identified patent and that said Letters Patent is hereby corrected as shown below:

In Claim 1, line 3, "carded" should read --carried--.

In Claim 10, line 2, "carded" should read --carried--.

Signed and Sealed this

Twenty-fifth Day of March, 1997

Attest:

BRUCE LEHMAN

*Attesting Officer*   *Commissioner of Patents and Trademarks*